(12) United States Patent
Kratoska et al.

(10) Patent No.: US 9,326,821 B2
(45) Date of Patent: May 3, 2016

(54) MEDICAL TUNNELING DEVICE AND METHOD

(75) Inventors: Paul S. Kratoska, Brooklyn Park, MN (US); Robert L. Olson, Vadnais Heights, MN (US); Bruce A. Behymer, Grant, MN (US); Alan O. Fung, Mansfield (AU)

(73) Assignee: MEDTRONIC, INC., Minneapolis, MN (US)

( * ) Notice: Subject to any disclaimer, the term of this patent is extended or adjusted under 35 U.S.C. 154(b) by 193 days.

(21) Appl. No.: 13/455,735

(22) Filed: Apr. 25, 2012

(65) Prior Publication Data

US 2012/0277760 A1    Nov. 1, 2012

Related U.S. Application Data

(60) Provisional application No. 61/480,599, filed on Apr. 29, 2011, provisional application No. 61/480,594, filed on Apr. 29, 2011.

(51) Int. Cl.
*A61B 19/00* (2006.01)
*A61N 1/05* (2006.01)
*A61B 17/32* (2006.01)

(52) U.S. Cl.
CPC .............. *A61B 19/201* (2013.01); *A61N 1/05* (2013.01); *A61B 2017/320056* (2013.01)

(58) Field of Classification Search
CPC ............. A61B 19/201; A61B 17/3401; A61B 2017/320056; A61N 1/05
USPC .......... 606/129, 1; 604/512; 601/36, 119, 131
See application file for complete search history.

(56) References Cited

U.S. PATENT DOCUMENTS

| | | | |
|---|---|---|---|
| 5,000,177 A * | 3/1991 | Hoffmann et al. | 607/2 |
| 5,314,464 A * | 5/1994 | KenKnight et al. | 607/132 |
| 5,782,841 A | 7/1998 | Ritz et al. | |
| 5,785,708 A * | 7/1998 | Betsill et al. | 606/43 |
| 5,865,842 A * | 2/1999 | Knuth et al. | 607/116 |
| 6,192,279 B1 * | 2/2001 | Barreras et al. | 607/117 |
| 6,475,244 B2 | 11/2002 | Herweck et al. | |
| 6,605,094 B1 * | 8/2003 | Mann et al. | 606/129 |
| 6,606,094 B1 * | 8/2003 | Jones, Jr. | 345/467 |
| 7,655,014 B2 | 2/2010 | Ko et al. | |
| 7,758,384 B2 * | 7/2010 | Alexander et al. | 439/623 |
| 2002/0095202 A1 * | 7/2002 | Schmidt | 607/122 |
| 2007/0191920 A1 * | 8/2007 | Ley et al. | 607/116 |
| 2008/0046056 A1 * | 2/2008 | O'Connor | 607/119 |
| 2008/0132980 A1 * | 6/2008 | Gerber | 607/118 |
| 2008/0221491 A1 * | 9/2008 | Slayton et al. | 601/3 |
| 2008/0243106 A1 * | 10/2008 | Coe et al. | 606/1 |
| 2010/0030227 A1 | 2/2010 | Kast et al. | |
| 2010/0063512 A1 * | 3/2010 | Braga et al. | 606/108 |
| 2011/0230893 A1 * | 9/2011 | Barker | 606/129 |
| 2012/0078268 A1 * | 3/2012 | Wahlstrand et al. | 606/129 |

* cited by examiner

*Primary Examiner* — Richard Louis
(74) *Attorney, Agent, or Firm* — Withers & Keys, LLC

(57) ABSTRACT

A medical device assembly includes a tunneler having a proximal end and a distal end and a carrier element fixed to the distal end of the tunneler. In various embodiments the carrier element is configured to be slidably disposed within a lead connection lumen. In various embodiments the carrier element includes a plurality of recesses configured to engage a lead extension set screw. In various embodiments the carrier element can freely rotate relative to the rest of the tunneler.

13 Claims, 11 Drawing Sheets

MEDICAL TUNNELING DEVICE AND METHOD

PRIORITY

This application claims the benefit of U.S. Provisional Application No. 61/480,599 entitled "MEDICAL TUNNELING DEVICE AND METHOD" filed on Apr. 29, 2011, and the benefit of U.S. Provisional Application No. 61/480,594 entitled "MEDICAL TUNNELING DEVICE WITH SWIVEL AND METHOD" filed on Apr. 29, 2011, the entire contents of each of which are incorporated herein by reference.

FIELD

This disclosure relates, inter alia, to implantable medical devices. More particularly, it relates to implantable medical devices and systems employing lead extensions and placement of implanted lead extensions with a tunneling device.

BACKGROUND

Placement of lead extensions in a patient may be required in a number of situations, such as placement of a medical device where the lead extension electrically connects an implantable electrical medical device to an electrical lead.

The use of lead extensions can serve multiple purposes. For example, lead extensions can electrically bridge the distance between a suitable implant site for an implantable pulse generator (IPG) and a lead implanted at tissue targeted for stimulation or sensing, where the lead alone may not be long enough. In some cases, an IPG may be implanted in the chest and a lead may be specifically configured to be implanted in the brain and accordingly the lead may be particularly thin and have external material suited for contacting brain matter. These design considerations may render the lead unsuitable for bridging a connection through the neck, as a lead that spans the neck may need to be durable, robust, extendable, and flexible enough to survive the everyday rotations, articulations, and extensions of the neck. In some cases, the lead extension may be specially configured to handle the neck environment (e.g., by being thicker and more flexible) while the lead may be specifically configured to handle the brain environment (e.g., thin enough to minimize interference with brain tissue and rigid enough to maintain implant position and orientation).

Implantation of lead extensions bridging the head and chest may be complicated by the lead extensions tangling when pulled though a subcutaneous tunnel between the head and chest. Tangling of the lead extension can increase the chances of the extension catching on something and/or requiring an increased pull force and/or a remedial surgical technique.

Sometimes carrier units are used to temporarily house a distal end connector of the lead extension to secure the lead extension to the tunneler and allow the tunneler to pull the lead extension through the subcutaneous tunnel. However, the carrier element in these cases wraps around distal end connector, which can make for a larger profile of the assembly as it is pulled through the subcutaneous tunnel, increasing resistance within the tunnel.

In some patients, resistance can be experienced while removing the tunneling device with the lead extension. Excessive force to remove the tunneling device with the lead extension can result in carrier failure.

SUMMARY

The present disclosure describes, among other things, apparatuses and methods that provide for robust placement of a lead extension in a patient.

Various embodiments concern a medical device assembly including a tunneler having a proximal end and a distal end and a carrier element fixed to the distal end of the tunneler. The carrier element is configured to be slidably disposed within a lead connection lumen. The carrier element includes a plurality of recesses configured to engage a lead extension set screw.

Various embodiments concern a medical device assembly including a tunneler having a proximal end and a distal end and a first and second carrier element fixed to the distal end of the tunneler. The first carrier element is configured to be slidably disposed within a first lead connection lumen. The first carrier element includes a plurality of recesses configured to engage a first lead extension set screw. The second carrier element is configured to be slidably disposed within a second lead connection lumen. The second carrier element includes a plurality of recesses configured to engage a second lead extension set screw.

Various embodiments concern a method comprising passing a tunneler from a first opening to a second opening in a patient, disposing a distal end carrier portion of the tunneler into a lead connection lumen of a lead extension, the lead extension having a set screw proximal to the lead connection lumen, and fixing the lead extension to the carrier portion with the set screw. The method includes pulling the tunneler and attached lead extension from the second opening to the first opening in the patient so that the lead extension extends between the second opening and the first opening in the patient, and removing the lead extension from the carrier portion. The method includes fixing the lead extension to the carrier portion with the set screw.

Various embodiments concern a method comprising: passing a tunneler from a first opening to a second opening in a patient, a subcutaneous tunnel being made by the passing of the tunneler; disposing a distal end carrier portion of the tunneler into a lead connection lumen of a lead extension, the lead extension having a set screw; fixing the lead extension to the distal end carrier portion with the set screw; pulling the tunneler and attached lead extension from the second opening to the first opening in the patient so that the lead extension extends between the second opening and the first opening in the patient; unfixing the lead extension from the distal end carrier portion with the set screw; removing the distal end carrier portion from the lead connection lumen; and connecting a lead to the lead extension by inserting a proximal end of the lead into the lead connection lumen and securing the lead to the lead extension with the set screw, the connecting of the lead to the lead extension completing at least one electrical connection between one or more electrical conductors of the lead extension and one or more electrodes on the distal end of the lead.

Some of the method embodiments further comprise removing a tunneling tip from the distal end of the tunneler after the passing step but before the disposing step, the tunneling tip configured to make the tunnel in subcutaneous tissue; and fixing the carrier portion to the distal end of the tunneler after the removing step.

In some of the method embodiments, fixing the lead extension to the distal end carrier portion comprises engaging the distal end carrier portion with the set screw; and unfixing the lead extension from the distal end carrier portion comprises disengaging the distal end carrier portion from the set screw.

In some of the method embodiments, the fixing step comprises fixing the lead extension to the distal end carrier portion with two or more set screws engaging the distal end carrier portion; and unfixing comprises releasing the two or more set screws from contact with the distal end carrier portion.

In some of the method embodiments, the tunneler creates one or both of the first opening and the second opening.

In some of the method embodiments, the distal end carrier portion comprises a first carrier element and a second carrier element, the first and second carrier elements connected to a common hub; the lead extension comprises a first lead extension having a first lead connection lumen and a second lead extension having a second lead connection lumen; the lead comprises a first lead having a proximal end and a distal end and a second lead having a proximal end and a distal end; disposing comprises disposing the first carrier element in the first lead connection lumen and disposing the second carrier element in the second lead connection lumen; and pulling the tunneler and attached lead extension comprises pulling the tunneler and both of the first and second lead extensions from the second opening to the first opening in the patient so that the first and second lead extensions extend between the second opening and the first opening in the patient; unfixing the lead extension comprises unfixing the first and second lead extensions from the first and the second carrier elements; removing the distal end carrier portion comprises removing the first and the second carrier elements from the first and the second lead extension lumens; and connecting the lead to the lead extension comprises inserting the proximal end of the first lead into the first lead connection lumen, securing the first lead to the first lead extension with a first set screw, inserting the proximal end of the second lead into the second lead connection lumen, and securing the second lead to the second lead extension with a second set screw.

Various embodiments concern a medical device assembly comprising: a lead having a proximal end and a distal end, the distal end having one or more electrodes on the distal end of the lead; a lead extension having a proximal end and a distal end, the distal end of the lead extension having a lead connection lumen and one or more electrical contacts, the lead and the lead extension configured such that the proximal end of the lead can be inserted into the lead connection lumen to complete at least one electrical connection between the one or more electrical contacts of the lead extension and the one or more electrodes of the lead, the lead extension configured to be securable to the lead when the proximal end of the lead is within the lead connection lumen; a tunneler having a proximal end and a distal end, the tunneler comprising a tip configured to make a subcutaneous tunnel, the tip either fixed or fixable to the distal end of the tunneler; and a carrier element either fixed or fixable to the distal end of the tunneler, wherein the carrier element is configured to be slidably disposed within the lead connection lumen and the lead extension is configured to be securable to the carrier element when the carrier element is within the lead connection lumen.

In some device embodiments, the lead extension comprises one or more set screws; the lead extension is configured to be securable to the carrier element by engagement between the one or more set screws and the carrier element; and the lead extension is configured to be securable to the lead by engagement between the one or more set screws and the proximal end of the lead.

In some device embodiments, the carrier element comprises one or more recesses and the lead extension comprises one or more set screws, wherein the lead extension is configured to be securable to the carrier element by engagement between the one or more set screws and the one or more recesses when the carrier element is within the lead connection lumen.

In some device embodiments, the one or more recesses comprises a plurality of recesses, the one or more set screws comprises a plurality of set screws, and the plurality of set screws and the plurality of recesses are configured such that the plurality of set screws respectively align with the plurality of recesses when the carrier element is within the lead connection lumen.

In some device embodiments, at least one of the one or more recesses has a planar bottom surface that is engaged by at least one of the one or more set screws. In some of the device embodiments, the carrier element is threadedly fixable to the distal end of the tunneler.

In some of the device embodiments, the carrier element is permanently fixed to the distal end of the tunneler.

In some of the device embodiments, the carrier element is an elongated rod.

In some of the device embodiments, the carrier element circumferentially fills the entire lead connection lumen when the carrier element is within the lead connection lumen.

In some of the device embodiments, the tip is configured to be removable from the tunneler.

In some of the device embodiments, the carrier element is able to be fixed to the tunneler only when the tip has been removed from the tunneler.

In some of the device embodiments, the tip is on a distal end of the carrier element.

In some of the device embodiments, the carrier element comprises a first carrier element and a second carrier element both fixed or fixable to the distal end of the tunneler; the lead extension comprises a first lead extension securable to the first carrier element and a second lead extension securable to the second carrier element; the lead connection lumen comprises a first lead connection lumen and a second lead connection lumen; and the first carrier element is configured to be slidably disposed within the first lead connection lumen and the second carrier element is configured to be slidably disposed within the second lead connection lumen to facilitate securement between the first lead extension and the first carrier element and between the second lead extension and the second carrier element.

In some of the device embodiments, at least a portion of the first carrier element and second carrier element are parallel extending elongated rods.

In some of the device embodiments, the first carrier element and the second carrier element are fixed to a common hub element and the common hub element is fixed or fixable to the distal end of the tunneler.

In some of the device embodiments, the first carrier element comprises one or more recesses; the first lead extension comprises one or more first lead extension set screws configured to respectively engage the one or more recesses of the first carrier element to facilitate securement between the first lead extension and the first carrier element; the second carrier element comprises one or more recesses; and the second lead extension comprises one or more second lead extension set screws configured to respectively engage the one or more recesses of the second carrier element to facilitate securement between the second lead extension and the second carrier element.

By providing the carrier portion of the tunneler that can be disposed into a lead connection lumen of a lead extension, a robust medical device assembly is formed and can place a lead extension in a patient while reducing the force required to withdraw the medical device assembly through the subcutaneous tunnel as compared to larger profile devices and techniques. These and various other features and advantages will be apparent from a reading of the following detailed description.

In various embodiments, a medical device assembly includes a tunneler having a proximal end and a distal end and a swivel element having a swivel proximal end and a swivel distal end. The swivel proximal end is fixed to the distal end of the tunneler and freely rotates about the distal end of the tunneler. The swivel distal end includes a male or female threaded end.

In some other embodiments, a medical device assembly includes a tunneler having a proximal end and a distal end and a swivel element having a swivel proximal end and a swivel distal end. The swivel proximal end is fixed to the distal end of the tunneler and freely rotates about the distal end of the tunneler. The swivel distal end includes a male or female threaded end. A medical device is threadedly attached to the swivel distal end.

Various embodiments concern a method of passing a tunneler from a first opening to a second opening in a patient. The tunneler includes a swivel element fixed to a distal end of the tunneler. The swivel element freely rotates about the distal end of the tunneler. The method includes rotating the swivel element to attach a medical device and pulling the medical device from the second opening to the first opening in the patient with the tunneler.

By providing the swivel element on the tunneler, a medical device (e.g., lead extension) can be easily and robustly attached to the swivel end and can place the medical device in a patient. The use of a swivel end in this manner can reduce twisting, deformation, and/or entanglement of the implanted lead extension thereby reducing the chance that a large pulling force will be required to withdraw the medical device assembly through the patient.

Various embodiments concern a medical device assembly for implanting an elongated lead element in a subcutaneous tunnel including a tunneler having a proximal end and a distal end, the tunneler configured to span the subcutaneous tunnel, a swivel element having a proximal end and a distal end, the proximal end rotatably fixed or fixable to the distal end of the tunneler and freely rotatable about the distal end of the tunneler, the distal end of the swivel element comprises a male or female threaded end, and a carrier element comprising a male or female threaded end configured to engage with the male or female threaded end of the swivel element, the carrier element configured to attach to the elongated lead element to securely link the elongated lead element to the tunneler, the swivel element configured to permit rotation between the carrier element and the tunneler. In some medical device assembly embodiments, the tunneler comprises either one of a male coupling element or a female connection element, and the swivel element comprises the other of the male coupling element or the female connection element, the male coupling element and the female connection element configured to slidably engage to connect the swivel element to the tunneler.

In some medical device assembly embodiments, the male coupling element comprises a recess or groove about a perimeter of the male coupling element and the female connection element comprises a detent configured to engage with the recess or groove and fix the swivel element to the tunneler while permitting rotation between the tunneler and the carrier element.

Some medical device assembly embodiments include a tunneling tip configured to make the subcutaneous tunnel. In some embodiments, the tunneling tip comprises a male or female threaded end configured to engage with the male or female threaded end of the swivel element, the tunneling tip configured to make the subcutaneous tunnel when attached to the distal end of the swivel element. In some embodiments, the tunneling tip is fixable to the distal end of the tunneler when the swivel element is not attached to the distal end of the tunneler.

In some medical device assembly embodiments, the carrier element comprises a holder, the holder configured to hold an end of the lead extension within the holder.

In some medical device assembly embodiments, the swivel element comprises a roughened or knurled exterior surface.

In some medical device assembly embodiments, the tunneler is a solid metal rod.

In some medical device assembly embodiments, the elongated lead element is a lead extension having a proximal end and a distal end, the proximal end configured to plug into an electrical implantable medical device and the distal end having a receptacle and a lumen, the lumen configured to accept a distal end of a lead.

Various embodiments concern a method of implanting an elongated lead element within a subcutaneous tunnel comprising: passing a tunneler from a first opening to a second opening in a patient, a subcutaneous tunnel being made by the passing of the tunneler, detaching a tunneling tip while a distal end of the tunneler extends out of the second opening, attaching a carrier element to a swivel element by twisting the swivel element, the swivel element connected to the tunneler, attaching the elongated lead element to the carrier element, the swivel element configured to securely link the elongated lead element to the tunneler while permitting rotation between the elongated lead element and the tunneler, and pulling the elongated lead element from the second opening to the first opening with the tunneler so that the elongated lead element extends from the second opening to the first opening in the subcutaneous tunnel.

In some method embodiments, detaching the tunneling tip comprising disengaging the tunneling tip from threading of the swivel element by twisting the swivel element, and attaching the carrier element to the swivel element comprises engaging the threading of the swivel element with threading of the carrier element.

In some medical device assembly embodiments, the tunneling tip is directly attached to the swivel element and the swivel element is directly attached to the tunneler during the passing step and detaching the tunneling tip comprises detaching the tunneling tip from the swivel element.

Some medical device assembly embodiments include connecting the swivel element to the tunneler.

In some medical device assembly embodiments, the tunneler comprises either one of a male coupling element or a female connection element and the swivel element comprises the other of the male coupling element or the female connection element, and connecting the swivel element to the tunneler comprises slidably engaging the male coupling element and the female connection element.

In some medical device assembly embodiments, connecting the swivel element to the tunneler comprises engaging a recess or groove about a perimeter of the male coupling element with a detent of the female connection element, the engagement of the recess or groove and the detent fixing the swivel element to the tunneler while permitting rotation between the tunneler and the swivel element. In some cases, the swivel element is not connected to the tunneler during the passing step and detaching the tunneling tip comprises detaching the tunneling tip from direct attachment to the tunneler.

In some medical device assembly embodiments, the carrier element comprises a first holder and a second holder; attaching the elongated lead element to the carrier element comprises inserting a portion of a first lead element into the first holder and inserting a portion of a second lead element into the second holder; and pulling the tunneler comprises pulling the first and the second lead elements from the second opening to the first opening in the patient so that the first and the second lead elements extend between the second opening and the first opening in the subcutaneous tunnel.

Some medical device assembly embodiments include making either or both of the first opening and the second opening with the tunneling tip. In some medical device assembly embodiments, the first opening is in the head region of the patient and the second opening is in the chest region of the patient.

In some medical device assembly embodiments, the elongated lead element comprises a lead extension having a proximal end and a distal end, and the method comprises: connecting a lead to the lead extension by inserting a proximal end of the lead into the distal end of the lead extension, and connecting the lead extension to an electrical implantable medical device by inserting the proximal end of the lead extension into the electrical implantable medical device.

Various embodiments concern a medical device for implanting an elongated lead element within a subcutaneous tunnel of a patient, comprising, a tunneler configured to span between a first opening in the patient and a second opening within the subcutaneous tunnel; a carrier element configured to attach to the lead extension; and means for linking the carrier element to the tunneler to allow the tunneler to pull the elongated lead element from the second opening to the first opening so that the elongated lead element extends from the second opening to the first opening in the subcutaneous tunnel while permitting free rotation between the carrier element and the tunneler, and for unlinking of the carrier element from the tunneler.

BRIEF DESCRIPTION OF THE DRAWINGS

The disclosure may be more completely understood in consideration of the following detailed description of various embodiments of the disclosure in connection with the accompanying drawings, in which.

Figure 1:
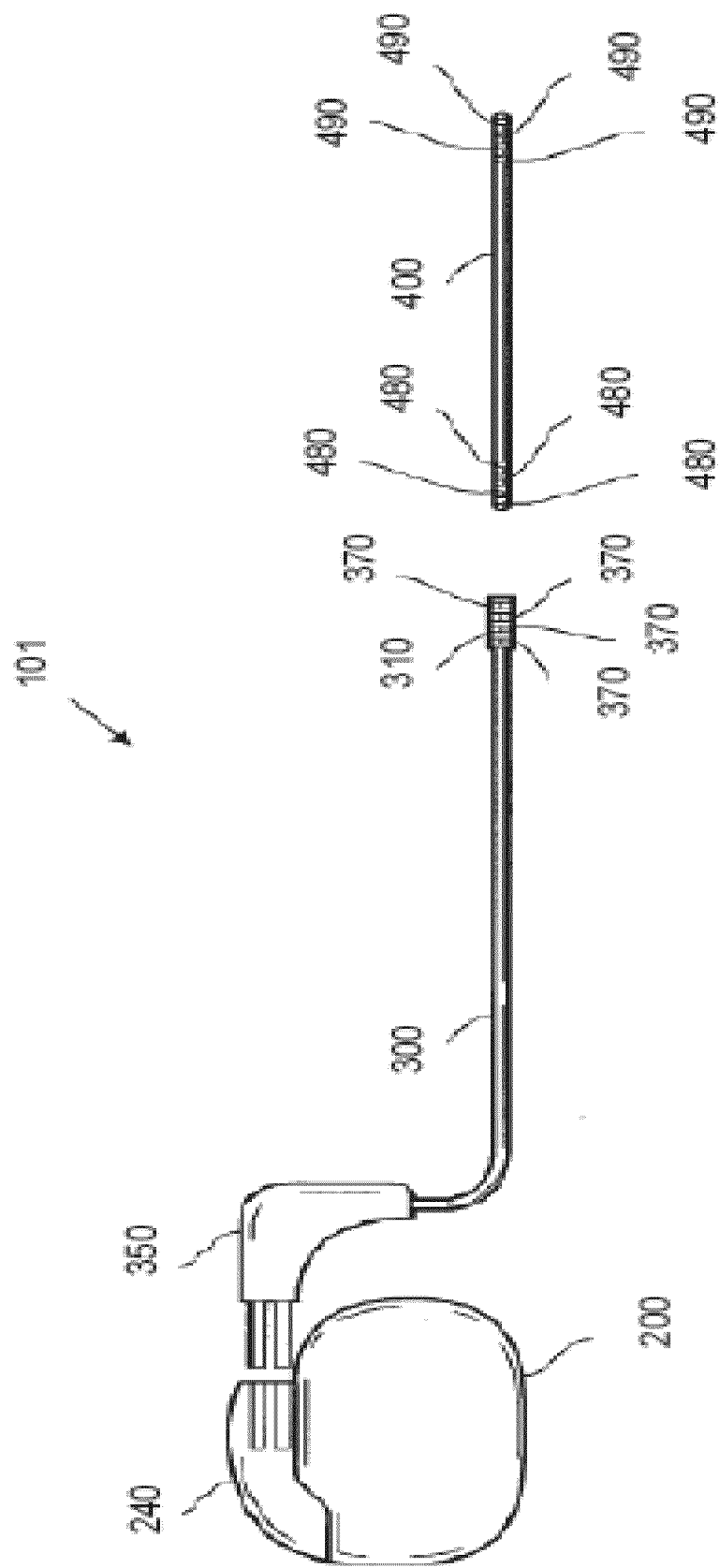
FIG. 1 is a schematic side view of a system including a lead extension for operably coupling a lead to an implantable electrical medical device.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Lead extensions can be placed in a patient by forcing a tunneling device through the patient body between two surgical openings in the body to form a subcutaneous tunnel (e.g., between the head and chest where a lead and IPG are respectively being implanted). Then a lead extension is disposed in a carrier on the tunneling device and pulled back through the subcutaneous tunnel, leaving the lead extension in the patient body and spanning the two surgical openings in the body. Then both the electrical lead and the active implantable electrical medical device can be electrically coupled to the lead extension to complete the procedure. As used herein, elongated lead element refers to one or both of a lead and a lead extension.

Resistance can be experienced as a result of engagement between the assembly and the walls of the subcutaneous tunnel. In particular, larger profile portions of the assembly can increase resistance. This includes embodiments where a lead extension is linked to a tunneler by a cradle that surrounds a portion of the lead extension. In some patients, resistance can be experienced while removing the tunneling device with the lead extension when the lead extension tangles within a subcutaneous tunnel. Enhanced force to remove the tunneling device with the lead extension can result in carrier failure.

The present disclosure describes, among other things, apparatuses and methods that provide for easy and robust attachment of a medical device to a tunneler and robust placement of the medical device (e.g., elongated lead element) in a patient. Some apparatuses and methods provide for robust placement of a lead extension in a patient while minimizing the profile moved through the subcutaneous tunnel. The apparatuses and methods described herein may be used in placing nearly any elongated lead element that is used with an implantable electrical medical device. A carrier element is disposed at a distal end of a tunneler. The carrier element is configured to be slidably disposed within a lead connection lumen and a fixation mechanism (e.g., a set screw, a spring mechanism such as a BAL SEAL™, wiper seal, frictional engagement member, shape memory engagement member, or other mechanism for fixing a lead end to a lead extension) of a lead extension is utilized to fix the lead extension to the carrier element. By providing the carrier portion of the tunneler that can be disposed within a lead connection lumen of a lead extension, a robust medical device assembly is formed that can pull an elongated lead element through a subcutaneous tunnel while minimizing the overall outer profile of the assembly within the subcutaneous tunnel. The carrier element of the tunneler and the lead extension can be unfixed by the fixation mechanism, such as disengagement between the set screw and the carrier element or overcoming the resistance or a seal or other engagement member. The carrier element can then be removed from the lead connection lumen and a proximal end of a lead can be inserted into the lumen and fixed to the lead extension with the fixation mechanism, such as a set screw or seal. The carrier element can also be fixed to two lead extensions to provide for placement of two lead extensions in the patient. While the present disclosure is not so limited, an appreciation of various aspects of the disclosure will be gained through a discussion of the examples provided below. Use of an internal carrier element to implant a lead extension is principally described herein, although it is noted that the disclosed apparatuses and methods can be applied to implantation of other elongated lead elements, such as a lead that is used with or without a lead extension.

Some embodiments concern a swivel element on the tunneler, where an elongated lead element can be robustly attached to the swivel end and can place the elongated lead element in a patient in a manner that minimizes the risk of lead entanglement during withdrawal of the medical device assembly through a subcutaneous tunnel in the patient. The swivel element can allow the elongated lead element to rotate independently of a tunneler handle and can reduce the possibility of entanglement. The swivel element can reduce the twists in the implanted lead extension and thus reduce residual stresses and latent reliability issues.

Lead extensions of any suitable system employing a lead extension for operably coupling a lead to an implantable electrical medical device or any other elongated lead element may be placed in accordance with the teachings presented herein. For example, a lead extension may be associated with an implantable medical device, such as a hearing implant; a cochlear implant; a sensing or monitoring device; a signal generator such as a cardiac pacemaker or defibrillator, a neurostimulator (such as a spinal cord stimulator, a brain or deep brain stimulator, a peripheral nerve stimulator, a vagal nerve stimulator, an occipital nerve stimulator, a subcutaneous stimulator, etc.), a gastric stimulator; or the like. For the purposes of convenience and brevity, the processes and apparatuses will be described in the context of replacement of a lead extension in a DBS system. However, it will be understood that the apparatuses and methods described herein may be employed with regard to replacement of any elongated lead element in nearly any implanted system.

Referring to FIG. 1, a schematic view of an example of an implantable electrical system 101 is shown. In the system shown in FIG. 1, implantable pulse generator (IPG) 200 includes a connector header 240 configured to receive male connector 350 at proximal end of lead extension 300. It will be understood that IPG 200 need not have a separate header 240 to receive extension 300. The distal end of extension 300 includes a lead receptacle 310 configured to receive proximal end of lead 400.

Receptacle 310 has internal electrical contacts 370 configured to electrically couple lead extension 300 to lead 400 via electrical contacts 480 disposed on the proximal end portion of lead 400. The receptacle 310 has a lead connection lumen that is configured to accept a proximal portion of the lead 400 and electrically couple to electrical contacts 480. The receptacle 310 has one or more lead extension set screws that are configured to fix the receptacle 310 to the lead 400.

Electrodes 490 are disposed on distal end portion of lead 400 and are electrically coupled to electrical contacts 480, typically through internal conductors (not shown). Lead 400 may include any number of electrodes 490, e.g. one, two, three, four, five, six, seven, eight, sixteen, thirty-two, or sixty-four. Typically, each electrode 490 is electrically coupled to a discrete electrical contact 480.

Figure 2:
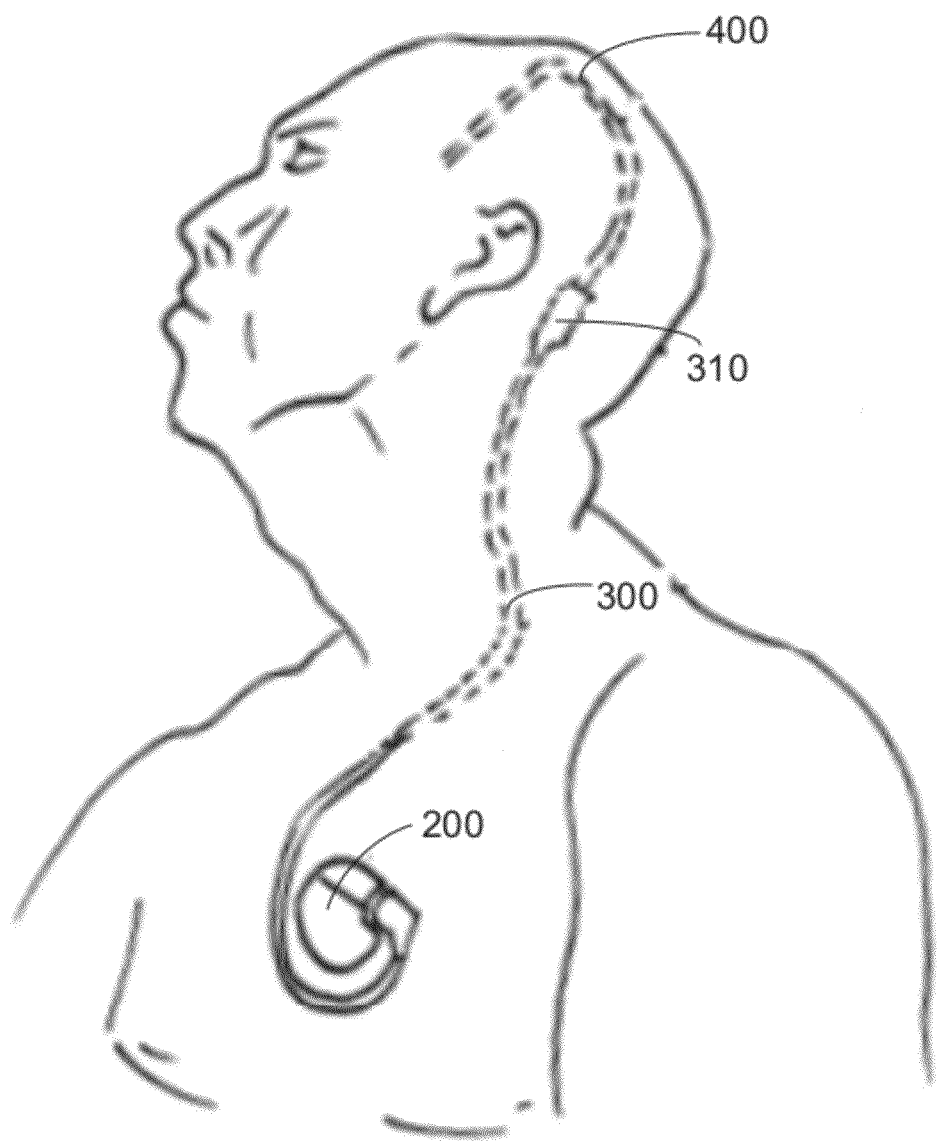
FIG. 2 is a schematic drawing of a system implanted in a patient, where the system includes a lead, a lead extension, and an implantable electrical medical device.

By way of example and referring to FIG. 2, a deep brain stimulation (DBS) system is shown implanted in a patient. For DBS, an IPG 200 can be placed in the abdominal region of patient, the cranial region, or in the pectoral region as shown. The IPG 200 may be placed in any medically acceptable location of the patient. The distal end of the lead 400 containing electrodes is placed at a desired location in the patient's brain. The proximal end of the lead 400 is inserted into a receptacle 310 of the lead extension 300, which is connected to the IPG 200. Once inserted, one or more lead extension set screws are engaged to fix the receptacle 310 to the lead 400. Thus, the lead extension 300 couples the lead 400 to the IPG 200. IPG 200 is capable of generating electrical signals that may be applied to tissue of a patient via the electrodes as part of therapy. It will be understood that a lead 400, lead extension 300, elongated lead element, or system may be used for purposes of applying electrical signals to tissue of a patient or for sensing signals from tissue of a patient.

Implantation of the lead extension 300 requires tunneling between a location in proximity to the location of a proximal end of the lead 400 to a location in proximity to the implant location of the IPG 200, which in the example of FIG. 2 includes tunneling from the head through the neck to the chest of the patient. A tunneling tool 100 is used to create a subcutaneous path between the implant location of the IPG 200 and implant location of the proximal end of the lead 400, the lead extension 300 being pulled through the tunneled path.

Figure 3:
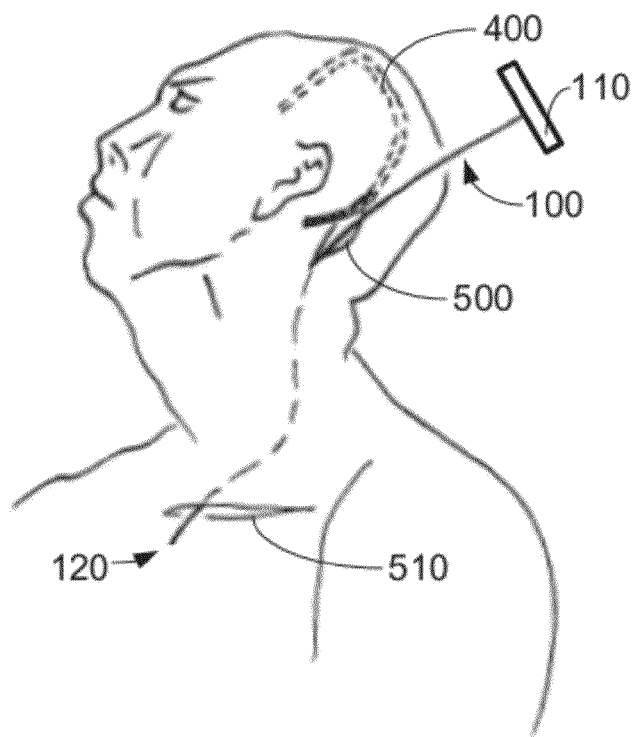
FIG. 3 is a schematic drawing of a tunneler inserted into a patient.

FIG. 3 is a schematic drawing of a tunneler 100 inserted into a patient. The tunneler 100 includes a handle 110 at a proximal end and a tunneling tip 120 connected to a distal end. The tunneling tip 120 forms the tunnel through the patient body between a first opening 500 (e.g., an incision) and a second opening 510. The tunneler 100 is inserted into the first opening 500 and forced through the patient body to the second opening 510. In some cases, the tunneler 100 is used to make either or both of the first opening 500 and the second opening 510 in some embodiments, a swivel element (described below) connects the tunneling tip 120 to the distal end of the tunneler 100.

In some embodiments, once the tunneling tip 120 exits the second opening or incision 510, the tunneling tip 120 is replaced with the lead extension carrier element 130. In some embodiments, the tunneling tip is the lead extension carrier element, as described below. The tunneler 100 is a relatively rigid rod or element that is stiff enough to be pushed through tissue to form the tunnel in the patient. However the tunneler 100 can be flexible enough to bend as required by the operator.

Figure 4:
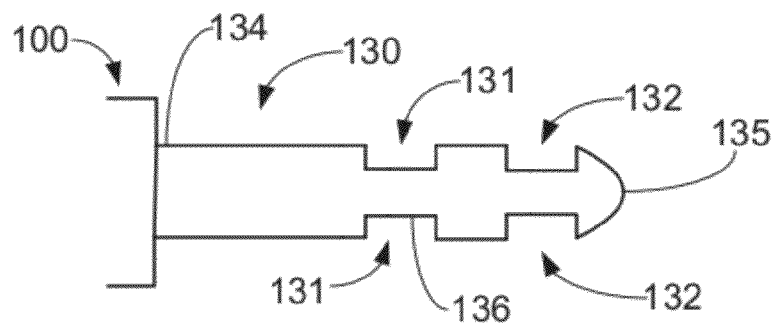
FIG. 4 is a schematic cross-sectional view of an illustrative carrier element.
Figure 5:
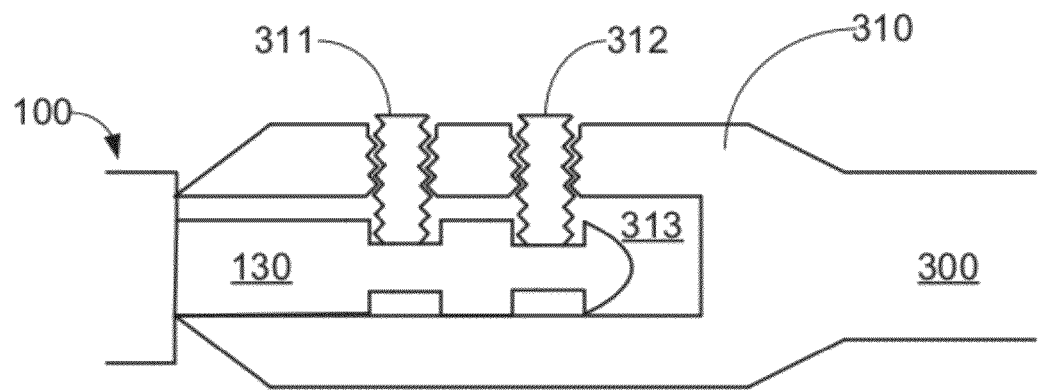
FIG. 5 is a schematic view of fixing the carrier element to the lead extension.
Figure 6:
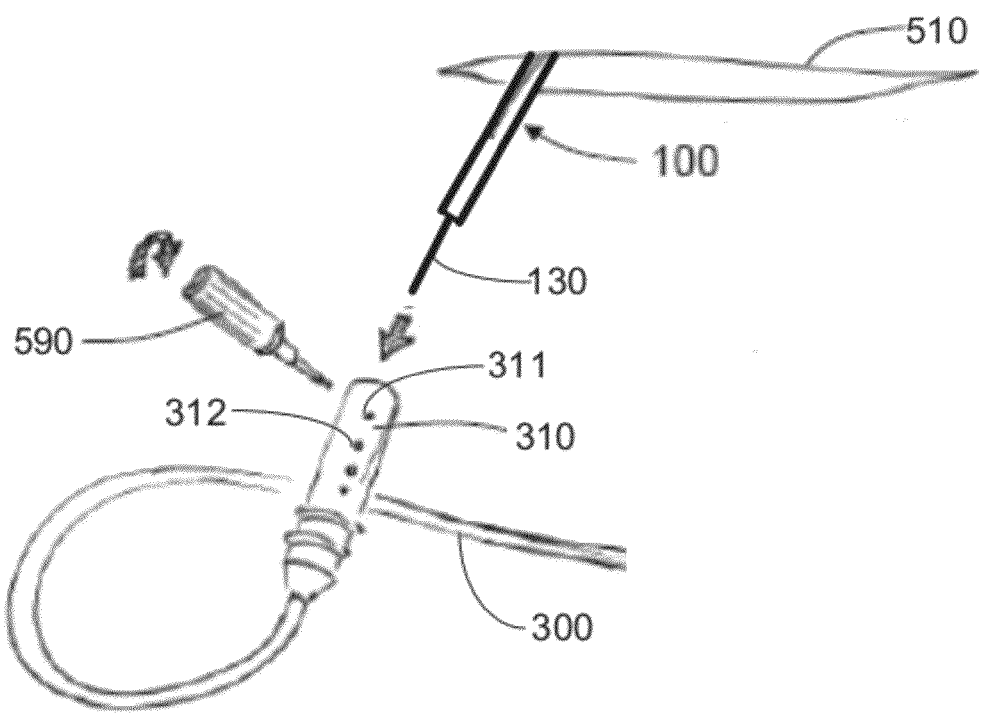
FIG. 6 is a schematic drawing of the carrier element being fixed to the lead extension.

FIG. 4 is a schematic cross-sectional view of an illustrative carrier element 130. FIG. 5 is a schematic view of fixing the carrier element to the lead extension. FIG. 6 is a schematic drawing of the carrier element 130 being fixed to the lead extension. The internal electrical contacts in the lead connection lumen 313 are not shown.

The lead extension carrier element 130 can be fixed to the tunneler 100 in any useful manner. In some embodiments the lead extension carrier element 130 can be threaded onto the tunneler 100 or the lead extension carrier element 130 can be threadedly fixed to the distal end of the tunneler 100.

In some embodiments, the lead extension carrier element 130 is fixed permanently to the tunneler 100. For example, the lead extension carrier element 130 and the tunneler 100 may be made from the same material (e.g., both machined from a metal rod or molded as a single polymer unit) or may be welded or adhered to one another. If the lead extension carrier element 130 is fixed permanently to the tunneler 100, then the carrier element 130 may comprise a distal tip 135 as a tunneling tip that has a point configured to make a subcutaneous tunnel or the carrier element 130 may be placeable over a tip of the tunneler that is configured to make the subcutaneous tunnel, where in the latter case the carrier element 130 may comprise a proximal end lumen to accommodate the tip of the tunneler 100 when the carrier element 130 is placed over the tip and attached (e.g., by threading) to the tunneler 100. The carrier element 130 is configured to be slidably disposed within a lead connection lumen 313. In some embodiments the lead extension carrier element 130 circumferentially fills the entire or substantially all of the lead connection lumen 313, circumferentially in that the width of the lead connection lumen 313 is occupied by the lead extension carrier element 130, although the entire length of the lumen is not necessarily filled by the lead extension carrier element 130. The lead extension carrier element 130 circumferentially filling the entire or substantially all of the lead connection lumen 313 can seal the distal mouth of the lumen to block bodily fluids from entering the lead connection lumen 313 when these components are brought through the tunnel and then are disengaged, which can protect electrical connections that are later established between electrical conductors on the proximal end of the lead 400 and within the lead connection lumen 313.

Once the carrier element 130 is disposed in the lead connection lumen 313, the carrier element 130 is fixed to the receptacle 310 of the lead extension 300 with one or more lead extension set screws 311, 312. A screwdriver 590 can be used to rotate the set screws 311, 312 and fix the carrier element 130 to the receptacle 310 of the lead extension 300.

The carrier element 130 can be an elongated rod that extends from a proximal end 134 to a distal tip 135. The proximal end 134 is fixed to the tunneler 100 and the distal tip 135 slides into the lead connection lumen 313. In some embodiments the carrier element 130 is an elongated rigid rod that is firmed from metal or stiff plastic.

The carrier element 130 includes a plurality of recesses 131, 132 that are configured to engage with the lead extension set screws 311, 312. In some embodiments, the plurality of recesses 131, 132 are placed along the length of the carrier element 130 so that they mate with one or more of the lead extension set screws 311, 312 when the carrier element 130 is fully disposed in the lead connection lumen 313.

In some embodiments the recesses 131, 132 have a planar bottom surface 136 that engages with the lead extension set screws 311, 312. While two recesses 131, 132 are illustrated, it is understood that any number of recesses are contemplated and can mate with and equal the number of lead extension set screws.

Once the lead extension set screws 311, 312 engage the plurality of recesses 131, 132 and fix the receptacle 310 of the lead extension 300 with the carrier element 130, then the tunneler 100 can be pulled back through the tunnel previously formed in the patient body from the second opening or incision 510 to the first opening or incision 500.

Figure 7:
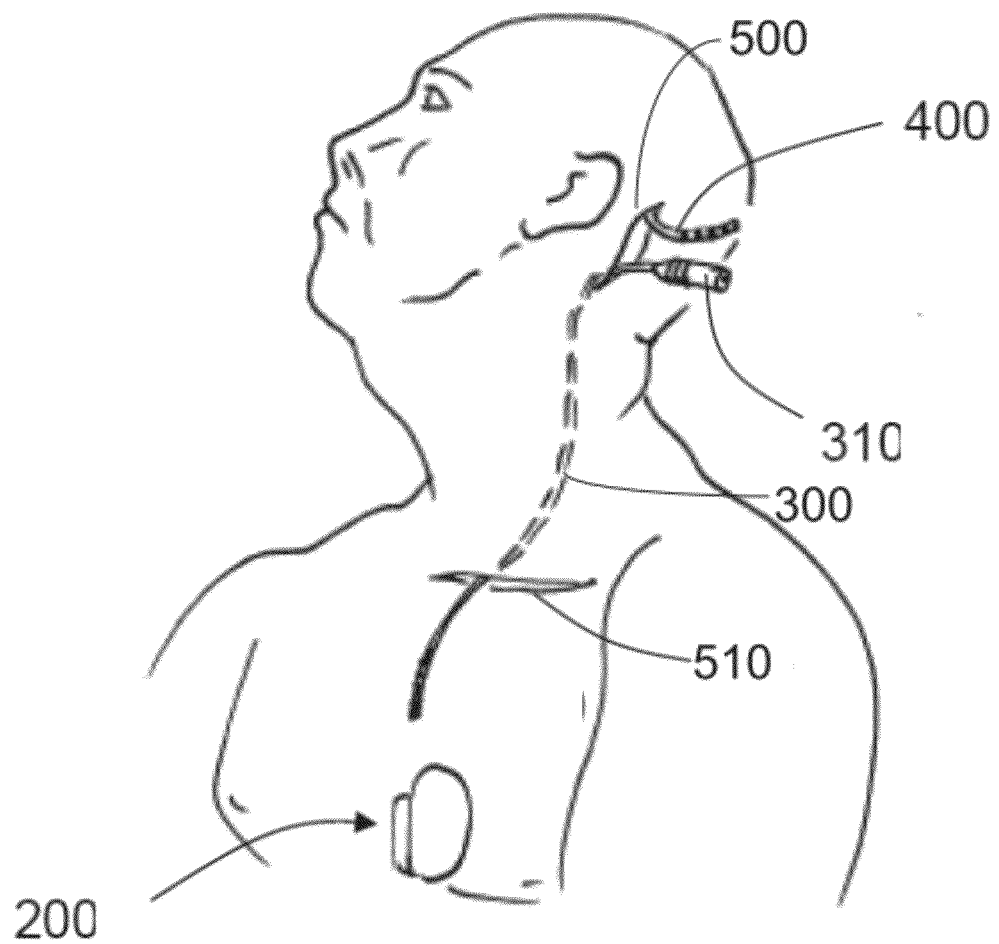
FIG. 7 is a schematic drawing of the lead extension placed into a patient spanning two surgical openings in the body with the tunneler.

FIG. 7 is a schematic drawing of the lead extension placed into a patient with the tunneler 100. The tunneler 100 is pulled from the patient through the first and second incisions 500, 510 drawing the lead extension 300 through the subcutaneous path previously occupied by the tunneler 100. The lead extension set screws are then disengaged from the plurality of recesses releasing the receptacle 310 of the lead extension 300 from the carrier element 130.

Then the lead 400 is connected to and secured within the lead receptacle 310 of the replacement lead extension 300 which has been pulled through the patient a sufficient distance to provide access to the lead receptacle 310 through the incision 500. The lead extension 300 can then be connected to the IPG 200. The IPG 200 and connected portions of the lead extension 300 may be implanted in the patient through the incision 510.

Figure 8:
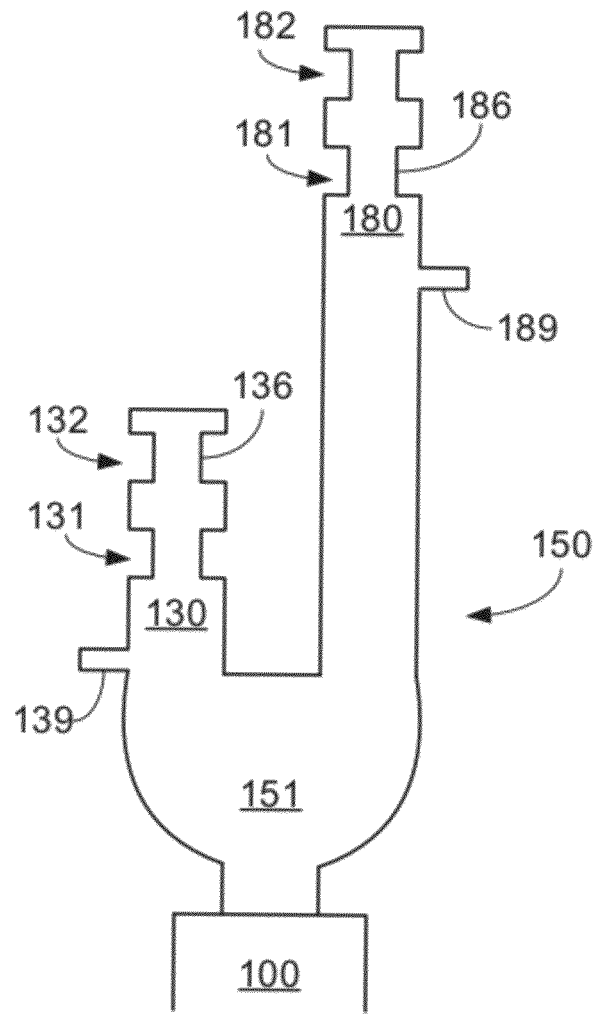
FIG. 8 is a schematic cross-sectional view of an illustrative dual carrier element.

FIG. 8 is a schematic cross-sectional view of an illustrative dual carrier element 150. The dual carrier element 150 can be fixed to the tunneler 100 in any useful manner, as described above. The dual carrier element 150 includes a first carrier element 130 and a second carrier element 180 fixed to a common hub 151. The common hub 151 fixes the dual carrier element 150 to the tunneler 100. The operation and function of the first carrier element 130 and a second carrier element 180 are the same as described above for the carrier element 130.

In some embodiments a first carrier element 130 and a second carrier element 180 are parallel extending elongated rods. In some embodiments the first carrier element 130 and a second carrier element 180 are laterally offset from one another so that the receptacle of each lead extension is laterally off-set from the other. This configuration can allow for a low-profile design and reduce a pulling force required to pull the lead extensions back through the subcutaneous tunnel.

The first carrier element 130 is configured to be slidably disposed within a first lead connection lumen. In some embodiments the first lead extension carrier element 130 fills the entire or substantially all of the first lead connection lumen. Once the first carrier element 130 is disposed in the first lead connection lumen, the first carrier element 130 is fixed to the receptacle of the first lead extension with one or more lead extension set screws, as described above.

The first carrier element 130 includes a plurality of recesses 131, 132 that are configured to engage with the first lead extension set screws, as described above. In some embodiments, the plurality of recesses 131, 132 are placed along the length of the first carrier element 130 so that they mate with one or more of the first lead extension set screws when the first carrier element 130 is fully disposed in the lead connection lumen. In some embodiments, the first carrier element 130 includes a stop element 139 that stops the advancement of the first lead extension on the first carrier element 130. The stop element 139 can be placed so that the plurality of recesses 131, 132 align with one or more of the lead extension set screws when the first lead extension is advanced onto the first carrier element 130 to the stop element 139. The embodiment of FIG. 4 could likewise include a stop element placed so that the plurality of recesses 131, 132 align with the lead extension set screws 311, 312 when the lead receptacle 310 is advanced onto the carrier element 130 to the stop element. In some embodiments similar to that of FIG. 4, the carrier element 130, recesses 131, 132, and proximal end 134 are spaced such that the lead receptacle 310 is stopped by contact with the proximal end 134 thereby aligning the plurality of recesses 131, 132 and the lead extension set screws 311, 312 when the carrier element 130 is slid into the lead receptacle 310.

In some embodiments the recesses 131, 132 have a planar bottom surface 136 that engages with the lead extension set screws, as described above. While two recesses 131, 132 are illustrated, it is understood that any number of recesses are contemplated and can mate with and equal the number of lead extension set screws.

The second carrier element 180 is configured to be slidably disposed within a second lead connection lumen. In some embodiments the second lead extension carrier element 180 fills the entire or substantially all of the second lead connection lumen. Once the second carrier element 180 is disposed in the second lead connection lumen, the second carrier element 180 is fixed to the receptacle of the second lead extension with one or more lead extension set screws, as described above.

The second carrier element 180 includes a plurality of recesses 181, 182 that are configured to engage with the second lead extension set screws, as described above. In some embodiments, the plurality of recesses 181, 182 are placed along the length of the second carrier element 180 so that they mate with one or more of the second lead extension set screws when the second carrier element 180 is fully disposed in the second lead connection lumen. In some embodiments, the second carrier element 180 includes a stop element 189 that stops the advancement of the second lead extension on the second carrier element 180. The stop element 189 can be placed so that the plurality of recesses 181, 182 align with one or more of the lead extension set screws when the lead extension is advanced onto the carrier element 180 to the stop element 189.

In some embodiments the recesses 181, 182 have a planar bottom surface 186 that engages with the lead extension set screws, as described above. While two recesses 181, 182 are illustrated, it is understood that any number of recesses are contemplated and can mate with and equal the number of lead extension set screws.

Once the lead extension set screws of both the first and second lead extensions engage the plurality of recesses 131, 132, 181, 182 and fix the receptacles of the first and second lead extensions with the carrier elements 130, 180 then the tunneler 100 can be pulled back through the tunnel previously formed in the patient body from the second opening or incision to the first opening or incision, leaving the first and second lead extensions in the subcutaneous tunnel spanning between the first opening or incision 500 and the second opening or incision 510.

Figure 9:
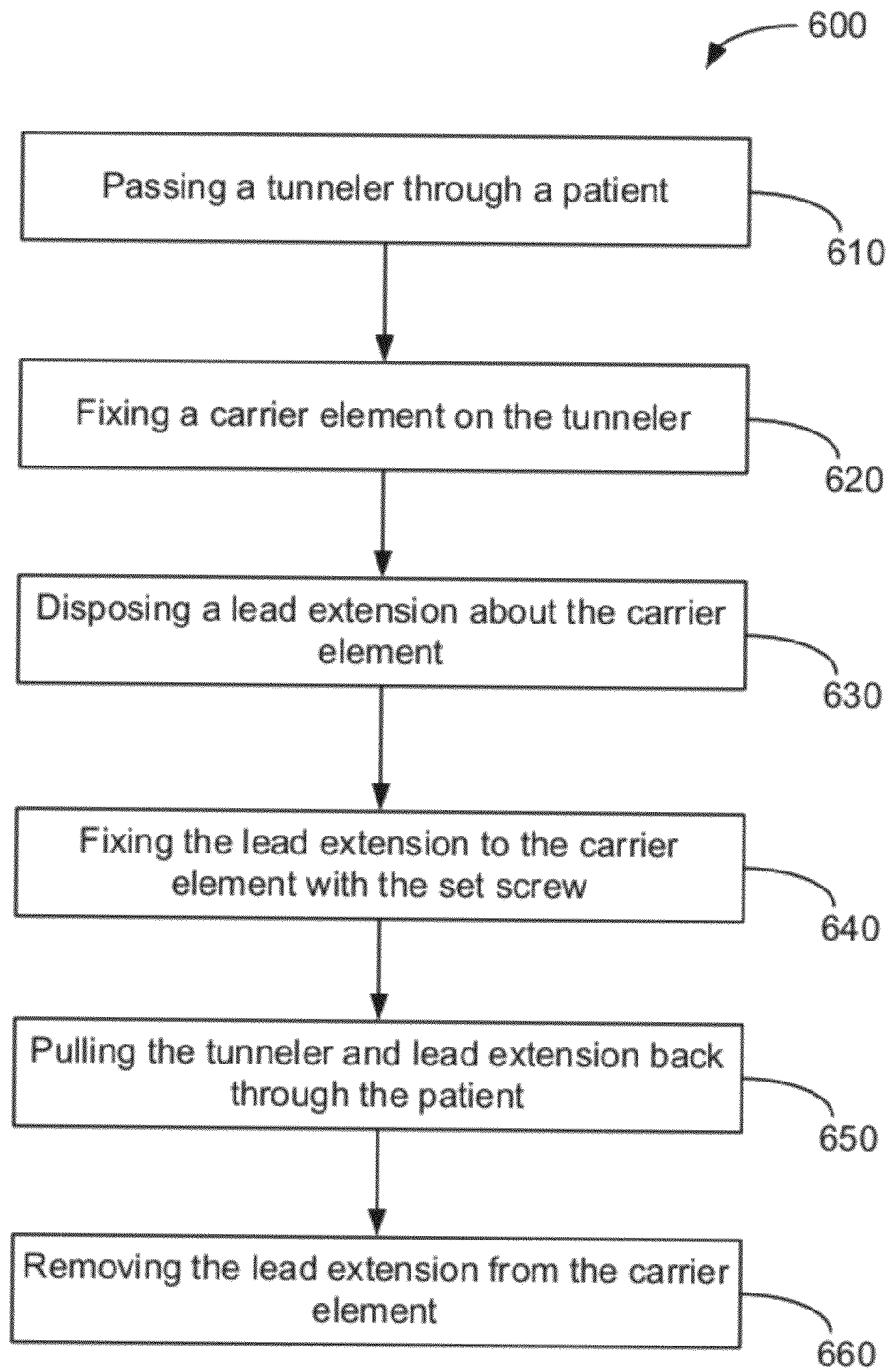
FIG. 9 is a flow diagram of an illustrative method.

FIG. 9 is a flow diagram of an illustrative method 600. The method for implanting a lead extension in a patient includes pushing or passing a tunneler from a first opening to a second opening in a patient at box 610. Then the method includes fixing a carrier portion or carrier element on a distal end of the tunneler at box 620. A tunneling tip can be removed from the tunneler and then the carrier portion can be fixed to the tunneler distal end by any useful manner, such as threading the carrier element or portion onto the tunneler. The carrier portion or element is configured to slide into the lead extension lumen.

The method includes disposing or sliding a lead connection lumen of a lead extension onto the carrier element at box 630 and fixing the lead extension to the carrier element with a set screw (or other fixation mechanisms) on the lead extension at box 640. The set screw (or other fixation mechanism) can align with a recess on the carrier element to securely fix the carrier element to the lead extension and provide a robust and secure connection; however it is noted that the carrier element may be generally straight (i.e. no recesses) in some embodiments and the set screw may be pressed onto the flat carrier element by screwing action to secure the carrier element to the lead extension by friction between the set screw and carrier element. The method then includes pulling the tunneler and secured lead extension from the second opening to the first opening in the patient at box 650 and removing the lead extension from the carrier portion at box 660 after set screws or other securement means have been released. A proximal end of a lead can then be inserted into the lead extension lumen. The lead can have a number of external contacts spaced on the proximal end of the lead that are electrically connected with electrodes on the distal end of lead. Inserting of the proximal end of a lead into the lead extension lumen can engage the contacts of the lead with electrical connectors within the lead extension lumen that are spaced to respectively connect with the contacts of the lead, thereby completing electrical connections between conductors of the extension and distal end electrodes of the lead. The set screws (or other fixation mechanisms) can again be engaged (e.g., screwed) in to fix the lead extension to the lead. In the case of set screws, the set screws apply pressure to the lead (e.g., on the contacts) or engaging a recess of the lead. The electrical connections may be made active when an IPG is connected to the proximal end of the lead extension and electrical energy is delivered from the IPG to the distal end electrodes of the lead for stimulation of tissue proximate the distal end electrodes.

If a dual carrier element is utilized (e.g., see FIG. 8) the method 600 includes disposing a distal end first carrier portion of the tunneler into a first lead connection lumen of a first lead extension and disposing a distal end second carrier portion of the tunneler into a second lead connection lumen of a second lead extension. The first carrier portion and the second carrier portion are fixed to a common hub and the common hub is fixed to the distal end of the tunneler. The first lead extension has a set screw proximal to the first lead connection lumen and the second lead extension has a set screw proximal to the second lead connection lumen.

In various embodiments, a swivel element can be employed on a tunneling tool. The swivel element can allow free rotation between the elongated lead element (e.g., a lead or extension) and a tunneling tool while the elongated lead element is withdrawing by the tunneling tool back through the patient. The swivel elements can allow the elongated lead element to confirm and move with the path of the tunnel and twist within the tunnel without building up twists within the elongated lead element. Specifically, the possibly irregular path of the tunnel may cause the elongated lead element to twist as the elongated lead element is brought through the tunnel. These twists can cause the elongated lead element to become wound up within the tunnel, causing stress and tension along the implanted lead. The swivel element can allow the elongated lead element to twist to conform to the possibly irregular path of the tunnel and ease the pulling of the elongated lead element through the tunnel without building up one or more twists of the lead material.

Various embodiments can have a swivel feature. Returning to FIG. 3, where the tunneling tip 720 exits the second opening 510, the tunneling tip 720 may be replaced with a swivel element that complements or is an alternative to the carrier element previously discussed. In some embodiments, the tunneling tip 720 is removed from the swivel element by holding the tunneling tip 720 and rotating the swivel element, where in this case the swivel element is permanently part of the tunneler 100.

Figure 10:
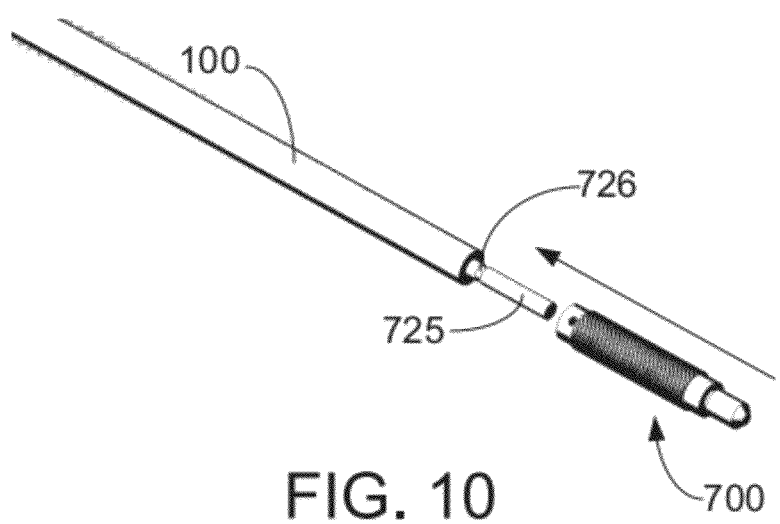
FIG. 10 is a schematic exploded perspective view of an illustrative swivel element and tunneler.
Figure 11:
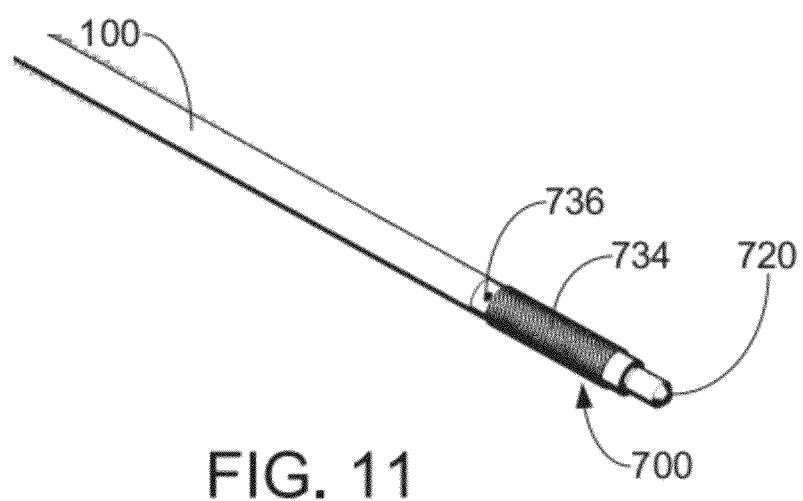
FIG. 11 is a schematic perspective view of the illustrative swivel element of FIG. 10 fixed to the tunneler.
Figure 12:
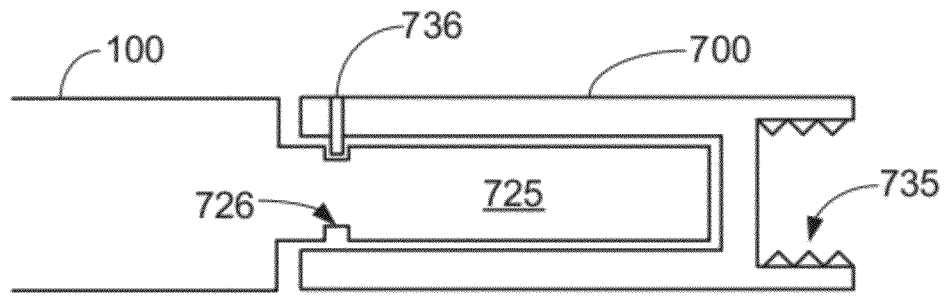
FIG. 12 is a schematic cross-sectional view of an illustrative swivel element fixed to the tunneler.

FIG. 10 is a schematic exploded perspective view of an illustrative swivel element 700 and tunneler 100. FIG. 11 is a schematic perspective view of the illustrative swivel element 700 of FIG. 10 fixed to the tunneler 100. FIG. 12 is a schematic cross-sectional view of an illustrative swivel element 700 fixed to the tunneler 100. A tunneling tip 720 is illustrated as being fixed to the distal end of the swivel element 700 in FIG. 10 and FIG. 11.

The swivel element 700 can be fixed to the distal end of the tunneler 100 via any useful manner that maintains axial rotation of the swivel element 700 relative to the tunneler 100 without the rotation separating the swivel element 700 from the tunneler 100 (e.g., not mere threading that can be unscrewed with a few turns). Generally, the swivel element 700 can rotate in both clockwise and counter-clockwise directions relative to the tunneler 100. In some embodiments the tunneler 100 includes a male coupling element 725 that has a reduced diameter relative to the tunneler 100 and a detent engagement recess or groove 726 about a perimeter of the male coupling element 725.

The swivel element 700 proximal end can include a female connection element that is configured to mate with the male coupling element 725 of the tunneler 100. The swivel element 700 can slidably engage the male coupling element 725. In some embodiments, a detent element 736 can engage the detent engagement recess or groove 726 of the male coupling element 725. The engagement of the detent element 736 with the detent engagement recess or groove 726 fixes the swivel element 700 to the tunneler 100 while allowing the swivel element 700 to rotate freely about the male coupling element 725 of the tunneler 100 (e.g., by having the recess or groove 726 extend all the way around (i.e. 360 degrees) the male coupling element 725). The outer surface 734 of the swivel element 700 can have a roughened surface or a knurled surface to assist in grasping and rotating the swivel element 700.

The tunneling tip 720 can be removed by rotating the swivel element 700 and disengaging the threaded end 735 of the swivel element 700 from the threaded end of the tunneling tip 720. The distal end of the swivel element 700 can include a threaded portion to threadedly engage a medical device, carrier element, or other medical element, as desired. The threaded portion can be a male threaded end or a female threaded end. FIG. 11 shows the tunneling tip 720 engaged with the swivel element 700 while FIG. 6 shows the swivel element 700 in a state where the tunneling tip 720 has been unthreaded from female threaded end 735 and removed from the swivel element 700.

Figure 13:
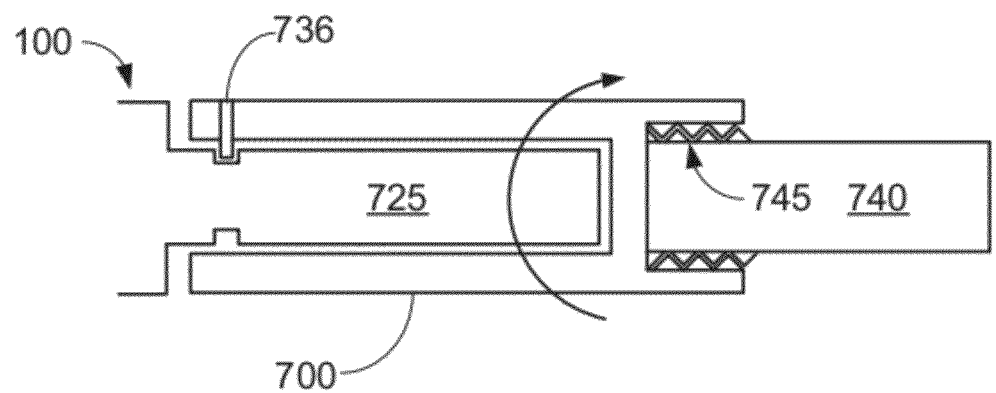
FIG. 13 is a cross-sectional view of an illustrative carrier element threadedly engaged with the swivel element.

FIG. 13 is a cross-sectional view of an illustrative carrier element 740 threadedly engaged with the swivel element 700. The carrier element 740 can be fixed to the distal end of the swivel element 700 by rotating (see arrow) the swivel element 700 relative to the carrier element 740. The illustrated embodiment shows a lead extension carrier element 740 having a male threaded end 745 threadedly engaged with a female threaded end 735 of the swivel element 700. In some other embodiments the carrier element 740 has a female threaded end threadedly engaged with a male threaded end of the swivel element 700.

Figure 14:
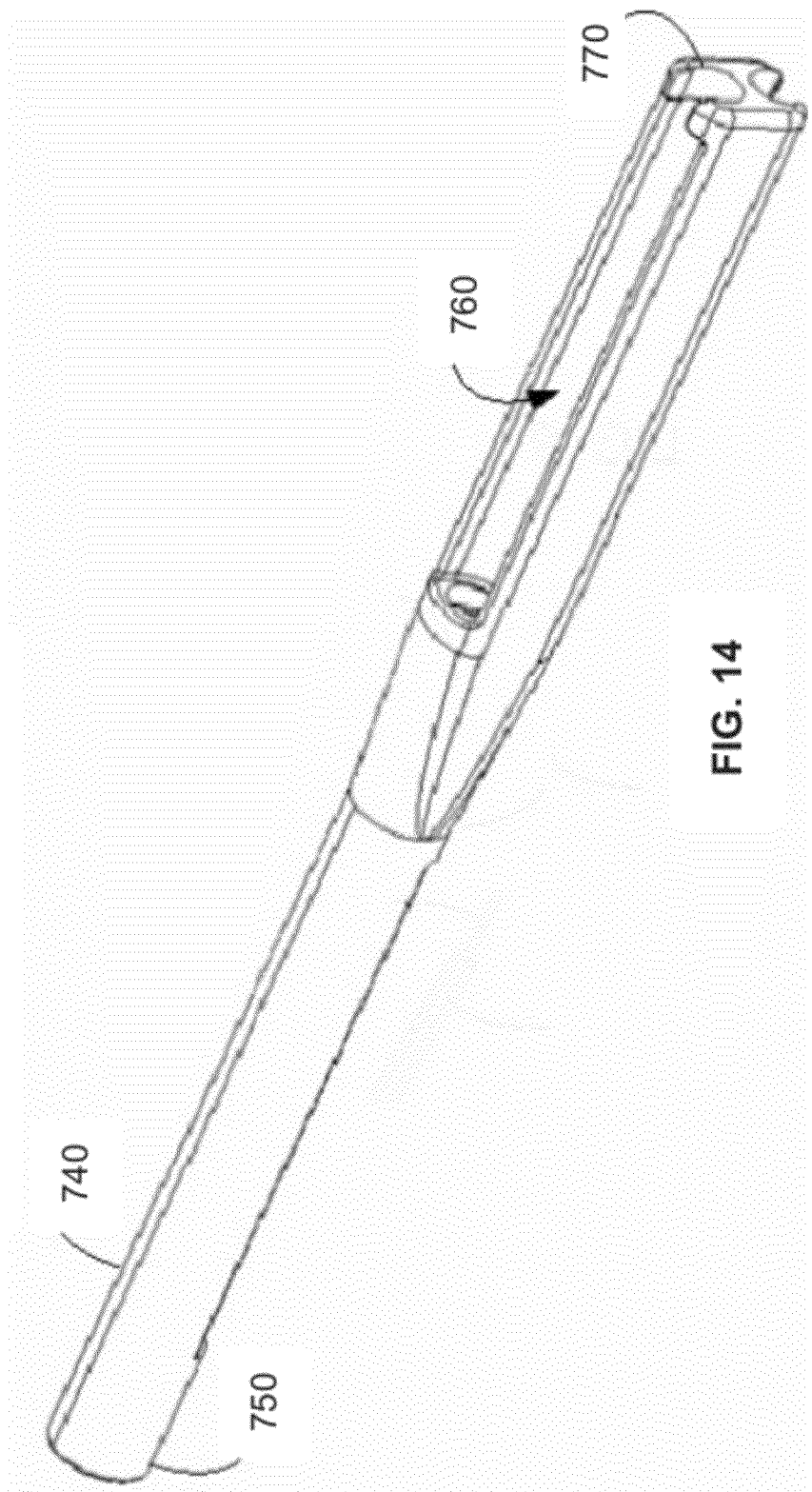
FIG. 14 is a schematic drawing of a carrier element.

FIG. 14 is a drawing of a carrier element 740. A proximal end 750 of the carrier element 740 can be threaded, as shown by male threaded end 745 in FIG. 13, to attach the carrier element 740 to the swivel element 700. In the embodiment of FIG. 14, the carrier element 740 includes a holder 760. The holder 760 interior is configured to fit an end of the lead extension 300, such as the lead receptacle 310 on the distal end of the lead extension 300 illustrated in FIG. 9, to secure the lead extension 300 to the carrier element 740 and thereby link the lead extension 300 to the swivel element 700 and the tunneler 100. The carrier element 740 includes a narrow end 770 which can be narrower than the width of the distal end of the lead extension 300 (the holder 760 being dimensioned to seat the lead receptacle 310) but wider than the elongated middle portion of the lead extension 300, allowing the elongated middle portion of the lead extension 300 to extend out of the narrow end 770 distally of the carrier element 740. In this way, the carrier element 740 can securely harness a distal end of the lead extension 300 and allow the rest of the lead extension 300 to be pulled behind the carrier element 740 as the tunneler 100 pulls the swivel element 700, carrier element 740, and lead extension 300 through a subcutaneous tunnel.

The carrier element 740 may contain multiple holder compartments for attaching multiple (e.g., two) lead extensions simultaneously and pulling both lead extensions through a subcutaneous tunnel. For example, a second holder can be included on the underside of the carrier element 740 proximal to the first holder 760, with the narrow end 770 including two narrowed sections for harnessing the respective distal ends of the two lead extensions while allowing the elongated middle sections of the lead extensions to extend from the carrier element 740. In some embodiments, the carrier element 740 is configured to be slidably disposed within a lumen of the distal end of the lead extension 300, such as a lumen in the receptacle 310. Once the carrier element 740 is disposed in the lumen, the carrier element 740 is fixed to the lead extension 300 with one or more lead extension set screws that screw down and engage the carrier element 740 or by some other fixation mechanism. In some embodiments the carrier element 740 is an elongated rigid rod that is formed from metal or stiff plastic.

Once the lead extension 300 is attached to the carrier element 740, then the tunneler 100 can be pulled back through the tunnel previously formed in the patient body from the second opening or incision 510 to the first opening or incision 500 such that the lead extension 300 spans between the first and the second openings. The receptacle of the lead extension 300 is then released from the carrier element 740 (e.g., removed from the holder 760) thereby uncoupling the tunneler 100 from the lead extension 300. The lead 400 can be connected to the lead extension 300 in the same manner as FIG. 7 or as otherwise described herein.

Figure 15:
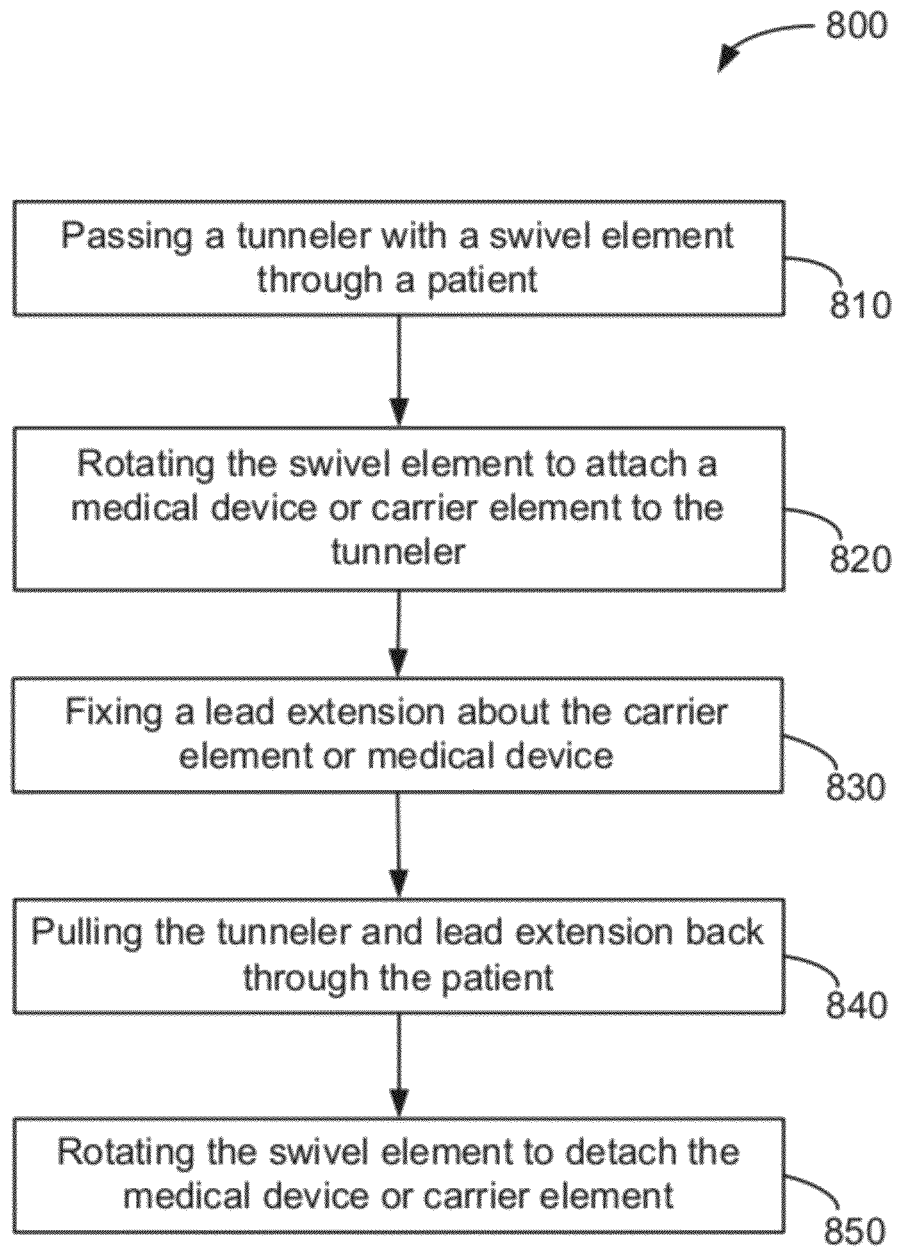
FIG. 15 is a flow diagram of an illustrative method.

FIG. 15 is a flow diagram of an illustrative method 800. The method 800 for implanting a lead extension in a patient includes pushing or passing a tunneler with a swivel element from a first opening to a second opening in a patient at box 810 to make a subcutaneous tunnel. A tunneling tip can be attached (e.g., by threaded engagement) to the distal end of the swivel element, the tunneling tip tapered to separate tissue and make the subcutaneous tunnel. In some embodiments, the swivel element is not attached to the tunneler during the pushing/passing step at box 810 and instead the tunneling tip is attached directly to the tunneler (e.g., by slidably engaging a female connection element with a male coupling element in similar manner to that of FIG. 15).

In some embodiments, a tunneling tip is removed from the distal end of the tunneler (e.g., by rotation to unthread a coupling between the tunneling tip and the swivel element) as the tunneling tip extends out of the second opening. Then, while the swivel element extends out of the second opening, the swivel element can be rotated to attach a carrier element to the tunneler at box 820. The method optionally includes fixing a lead extension about the carrier element at box 830. The method includes pulling the lead extension from the second opening to the first opening in the patient with the tunneler and swivel element at box 840. The method optionally includes rotating the swivel element to detach the swivel element from the carrier element from the tunneler at box 850.

Thus, embodiments of the MEDICAL TUNNELING DEVICE AND METHOD are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:

1. A medical device assembly comprising:
   a lead having a proximal end and a distal end, the distal end having one or more electrodes;
   a second lead having a proximal end and a distal end, the distal end of the second lead having one or more electrodes;
   a lead extension having a proximal end and a distal end, the distal end of the lead extension having a lead connection lumen and one or more electrical contacts, the lead and the lead extension configured such that the proximal end of the lead can be inserted into the lead connection lumen to complete at least one electrical connection between the one or more electrical contacts of the lead extension and the one or more electrodes of the lead, the lead extension configured to be securable to the lead when the proximal end of the lead is within the lead connection lumen;
   a second lead extension having a proximal end and a distal end, the distal end of the second lead extension having a lead connection lumen and one or more electrical contacts, the second lead and the second lead extension configured such that the proximal end of the second lead can be inserted into the second lead connection lumen to complete at least one electrical connection between the one or more electrical contacts of the second lead extension and the one or more electrodes of the second lead, the second lead extension configured to be securable to the second lead when the proximal end of the second lead is within the lead connection lumen of the second lead extension;
   a tunneler having a proximal end and a distal end, the tunneler comprising a tip configured to make a subcutaneous tunnel, the tip either fixed or fixable to the distal end of the tunneler; and
   a carrier element comprising a hub either fixed or fixable to the distal end of the tunneler, wherein the hub comprises a first carrier element having a first length and a second carrier element having a second length greater than the first length with the first and second carrier elements being laterally spaced apart so as to extend longitudinally in a parallel configuration, the lead extension being secured to the first carrier element and the second lead extension being secured to the second carrier element, the first carrier element is configured to be slidably disposed within the lead connection lumen and the second carrier element is configured to be slidably disposed within the second lead connection lumen to facilitate securement between the lead extension and the first carrier element and between the second lead extension and the second carrier element.

2. The medical device assembly according to claim 1, wherein:
   the lead extension comprises one or more set screws;
   the lead extension is secured to the carrier element by engagement between the one or more set screws and the carrier element; and
   the lead extension is configured to be securable to the lead by engagement between the one or more set screws and the proximal end of the lead.

3. The medical device assembly according to claim 1, wherein the carrier element comprises one or more recesses and the lead extension comprises one or more set screws, wherein the lead extension is secured to the carrier element by engagement between the one or more set screws and the one or more recesses when the carrier element is within the lead connection lumen.

4. The medical device assembly according to claim 3, wherein the one or more recesses comprises a plurality of recesses, the one or more set screws comprises a plurality of set screws, and the plurality of set screws and the plurality of recesses are configured such that the plurality of set screws respectively align with the plurality of recesses when the carrier element is within the lead connection lumen.

5. The medical device assembly according to claim 4, wherein the plurality of set screws are equally spaced to align with a plurality of metal contacts on a proximal end of the lead when the proximal end of the lead is within the lead connection lumen, the plurality of set screws being configured to engage the plurality of metal contacts to secure the lead to the lead extension.

6. The medical device assembly according to claim 4, wherein at least one of the one or more recesses has a planar bottom surface that is engaged by at least one of the one or more set screws.

7. The medical device assembly according to claim 1, wherein the carrier element is threadedly fixable to the distal end of the tunneler.

8. The medical device assembly according to claim 1, wherein the carrier element is permanently fixed to the distal end of the tunneler.

9. The medical device assembly according to claim 1, wherein the carrier element circumferentially fills the entire lead connection lumen when the carrier element is within the lead connection lumen.

10. The medical device assembly according to claim 1, wherein the tip is configured to be removable from the tunneler.

11. The medical device assembly according to claim 10, wherein the carrier element is able to be fixed to the tunneler only when the tip has been removed from the tunneler.

12. The medical device assembly according to claim 1, wherein the tip is on a distal end of the carrier element.

13. A medical device assembly comprising:
   a lead having a proximal end and a distal end, the distal end having one or more electrodes;
   a lead extension having a proximal end and a distal end, the distal end of the lead extension having a lead connection lumen and one or more electrical contacts, the lead and the lead extension configured such that the proximal end of the lead can be inserted into the lead connection lumen to complete at least one electrical connection between the one or more electrical contacts of the lead extension and the one or more electrodes of the lead, the lead extension configured to be securable to the lead when the proximal end of the lead is within the lead connection lumen;

a tunneler having a proximal end and a distal end, the tunneler comprising a tip configured to make a subcutaneous tunnel, the tip fixable to the distal end of the tunneler;

a carrier element fixable to the distal end of the tunneler, wherein the carrier element is configured to be slidably disposed within the lead connection lumen and the lead extension is configured to be securable to the carrier element when the carrier element is within the lead connection lumen; and a swivel element having a detent element and having a swiveling engagement with the tunneler where the detent element engages a groove that forms a circle about the distal end of the tunneler, the swivel element having a threaded engagement with the fixable tip and the fixable carrier element, wherein the swiveling engagement provided by the detent element engaged with the groove allows the lead extension to freely rotate relative to the tunneler when the carrier element is fixed via the threaded engagement to the swivel element and the lead extension is secured to the carrier element.

* * * * *